United States Patent [19]

Kay

[11] Patent Number: 4,884,463
[45] Date of Patent: Dec. 5, 1989

[54] TESTING APPARATUS

[75] Inventor: Joseph B. Kay, Berkshire, Great Britain

[73] Assignee: Microspan Process Controls Limited, Great Britain

[21] Appl. No.: 177,683

[22] Filed: Apr. 5, 1988

Related U.S. Application Data

[63] Continuation-in-part of Ser. No. 42,942, filed as PCT GB86/00429 on Jul. 21, 1986, published as WO87/0062 on Jan. 29, 1987, abandoned.

[30] Foreign Application Priority Data

Jul. 19, 1985 [GB] United Kingdom ............... 8518305

[51] Int. Cl.⁴ .................................................. G01B 5/06
[52] U.S. Cl. ................................ 73/865.8; 198/339.1
[58] Field of Search ............... 73/865.8, 821; 222/266; 414/223, 744 R; 198/479.1, 480.1, 481.1, 339.1; 193/341

[56] References Cited

U.S. PATENT DOCUMENTS 4,388,989 6/1983 Edmunds et al. ................... 198/339
4,393,717 7/1983 Mason et al. ......................... 73/821
4,472,960 9/1984 Motoyama et al. ..................... 73/7

FOREIGN PATENT DOCUMENTS 1241327 5/1967 Fed. Rep. of Germany ... 198/479.1
2017305 10/1979 United Kingdom .

Primary Examiner—Robert R. Raevis
Attorney, Agent, or Firm—Ostrolenk, Faber, Gerb & Soffen

[57] ABSTRACT

Cylindrical tablets are tested on a circular testing table by first weighing, then adjusting their position relative to a part of the table pushing them round the circular path in response to the weight measurement, then measuring their thickness and finally testing their crushing strength. The table has radial slots with a concave (preferably V-shaped) outer portion for urging the tablets round the circular path.

8 Claims, 6 Drawing Sheets

TESTING APPARATUS

BACKGROUND OF THE INVENTION

This is a continuation-in-part of application Ser. No. 042,942 filed as PCT GB86/00429 on Jul. 21, 1986, published as WO87/00621 on Jan. 29, 1987, now abandoned.

When it is desired to convey articles in a circular path between various testing stations the articles can be pushed by a conveyor rotating about the center of the circular path and kept at the desired distance from the center by a stationary circular guide member. Alternatively, the conveyor can be provided with receptacles in which the articles are placed. The first of these methods has the disadvantage of friction between the stationary guide and the articles to be conveyed, and the second has the disadvantage that the receptacles in the conveyor are difficult to make and it is difficult to place the articles in the receptacles and remove them therefrom.

SUMMARY OF THE INVENTION

According to one aspect of the invention there is provided a conveyor for moving articles in a circular path, the conveyor comprising a disc formed with radial slots, the side of each slot which will be located behind the article when the disc is rotated in a given direction being concave with a outer portion having a component facing towards the center of the disc. The concave shape of the slot side is preferably V-shaped.

According to another aspect of the invention there is provided apparatus for measuring the thickness of an article comprising a sensor arranged to be moved into contact with the article, means for measuring the weight of the article, means for adjusting, i.e. indexing, the position of the article relative to said sensor in response to the weight measuring means and means for measuring the position of the sensor when in contact with the article. With this arrangement, the radial size of the article can be calculated from the weight measurement when its density and standard thickness are known, and when the article is moved to the thickness measuring station transversely to the movement of the thickness sensor by pushing on the side of the article, the distance moved can be adjusted according to the radial size calculation so that the thickness sensor is moved into contact with the center of the article. This is particularly useful when measuring the thickness of cylindrical tablets whose end faces are non-planar, e.g. dished.

The invention further provides a tablet alignment apparatus for aligning tablets which have a longitudinal axis. The alignment apparatus has a conveyor disc and a ram, the conveyor disc having at least one generally radial slot open to the circumference of the disc and dimensioned to receive a tablet therein and to enable the ram to reciprocate in the slot. The radial slot is bounded by one planar radial side, a base and a convex radial side. The arrangement is such that the longitudinal axis of the tablet can be aligned radially between the base of the slot and the ram. Preferably, the convex radial side of the slot is V-shaped.

The tablet aligning apparatus may comprise further an index table and an index member for aligning a tablet which has two parallel flat surfaces that are interconnected by two convex surfaces. The operative surface of the index table has two step portions which successively raise the height of the table in a direction of intended relative travel of the tablet over the table. The minimum operative separation between the index member and the table and the respective heights of the steps are such as to assure that regardless of whether the initial orientation of the tablet is with a flat surface or a convex surface in contact with the table, in the final step the tablet will be positioned such that one of its convex surfaces is in contact with the table.

Preferably, a thickness gauge is also provided for reciprocating toward and away from the top surface of the tablet in the final step, whereby the thickness of the tablet across its convex surfaces may be measured.

The aforementioned thickness measuring apparatus for measuring the thickness dimension of an article having thickness and radial dimensions, may be configured to include a sensor arranged to be moved along the thickness dimension to contact the article. A centering means is effective for centering the article, i.e. the tablets, under the sensor, the centering means including: a) a weighing means for weighing the article and for producing a measured weight thereof; and b) calculating means for calculating a radial dimension for each of the articles on the basis of the measured weight and a standard thickness associated with the article.

The calculated radial dimension of the article then enables the article to be positioned precisely such that it will be centered under the sensor. preferably, the calculating means calculates the value of the radial dimension by reference to the square root of the measured weight.

The apparatus preferably has a plurality of processing stations including one station where the sensor is located and another for the weighing means. A conveyor moves the tablets in a circular path from one processing station to another, the conveyor including a disc formed with radial slots wherein each slot has a pushing edge for pushing a tablet located in the slot when the disc is rotated in a forward direction. Each of the slots further has a concave portion suitable for engaging the tablet therewith and an inward facing portion which forms part of the concave portion for retaining the tablet in the slot and entraining it to move along the circular path.

The conveyor disc is movable step-wise, in an indexed fashion, by means of a suitable driving mechanism comprising, for example, a stepper motor or the like. Consequently, each of the tablets will be moved step-wise from one processing station to another with the conveyor disc pausing at each processing station to complete the test or measurement that are performed at the particular processing station.

Other features and advantages of the present invention will become clear from the following description of the invention which is set forth by referring to the following drawings.

DETAILED DESCRIPTION OF THE DRAWINGS

Figure 1:
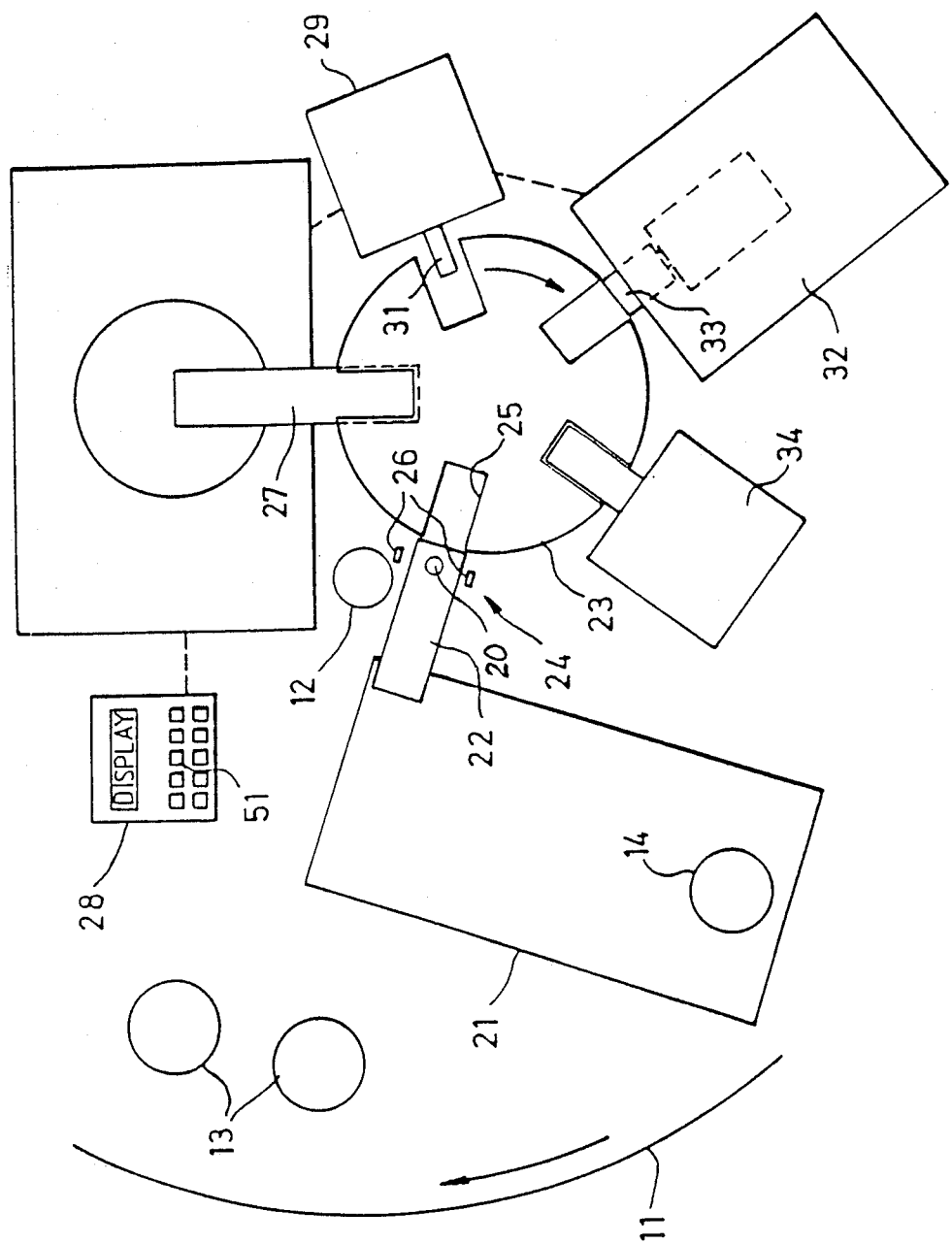
FIG. 1 is a schematic diagram of tablet testing apparatus.
Figure 1A:
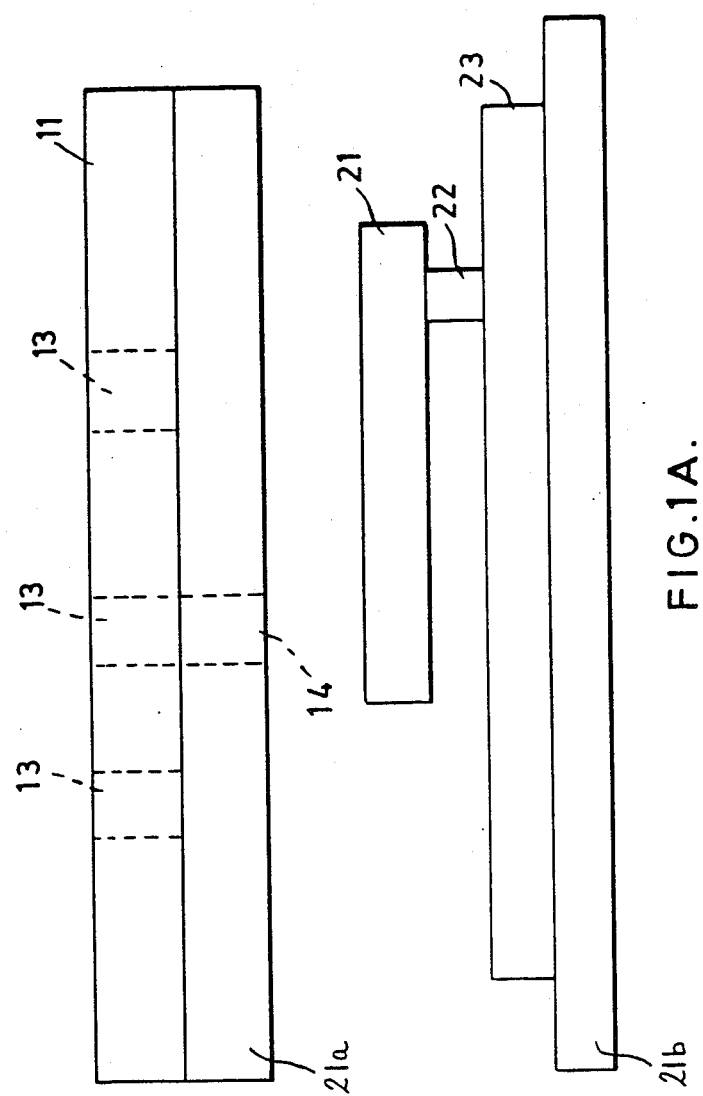
FIG. 1A is an elevational cross-section of the testing apparatus of FIG. 1, and shows tables that are present in the apparatus.

An upper conveyor disc 11 rotates about a shaft 12 and is formed with a plurality of holes 13, each of which can contain a quantity of coaxial tablets, such as 20 tablets. The disc 11 rotates over a first table 21a (FIG. 1A) which is formed with a hole 14 aligned with the holes 13. With this arrangement the contents of each hole 13 are deposited through the hole 14 as the disc 11 rotates about the shaft 12, the tablets falling onto a vibrating table 21 which passes them in a single file onto a moving belt 22. The belt 22 is radially aligned with a conveyor disc 23 which rotates over a second and fixed table 21b (FIG. 1A) and is formed with a plurality of equally spaced radial slots 25 (in the illustrated example there are 5 slots). Equally spaced around the outside of the disc are an equal number of processing stations. The shape of the slots 25 is only shown schematically in FIG. 1; the shape is accurately shown in and described with reference to FIG. 2.

At the first processing station 24 which is a loading station a photoelectric detector 26 responds to the passage of a tablet 20, past the detector into the adjacent aligned slot 25 of the disc by stopping the belt. The disc 23 is then rotated so that the first slot is aligned with a weighing device 27 at the second processing station. At the same time, the belt 22 is restarted until a further tablet has passed the detector 26 into the next slot which is now aligned with the belt 22 at the loading station.

At the weighing station 27, the tablet has been pushed by the conveyor disc onto the platform of weighing apparatus and the weight measurement is recorded in a microprocessor 28. When the weight measurement has been made and recorded, the disc rotates again, so that the first tablet passes to a thickness gauge 29 at which a sensing device 31 is lowered onto the tablet and measures its height above the stationary table over which the disc 23 rotates. The thickness measurement is made and recorded in the microprocessor 28. The disc 23 then rotates again to align the tablet with a hardness tester 32 at which a crushing ram 33 applies an increasing crushing force to the side of the tablet and measures the force at which the tablet crushes. This force is measured and recorded in the microprocessor 28. The disc rotates to the final station 34 where the crushed tablet is pressed from the slot in the disc to an output chute in the base table.

With five processing stations, the disc 23 rotates through a nominal 72° between stations. This nominal angle is varied in two ways. Firstly, the rotation includes the forward movement followed by a small backward movement so as to withdraw the trailing edge of the radial slot of the disc 23 from contact with the tablet at each station. This is important at the weighing station since friction with the disc 23 must not hinder movement of the tablet on the weighing platform and so make the weight measurement inaccurate. Secondly, the weight measurement is used to calculate the radius of the cylindrical tablet given its density and a standard thickness, and this radius is used to adjust the movement of the disc 23 in proportion to the square root of the weight measurement, since the weight is proportional to the product of the cross sectional area times the thickness, so that the tablet is moved to a position with its center exactly under the sensor 31 so that it is thickness at the exact center of the tablet which is measured.

Figure 2:
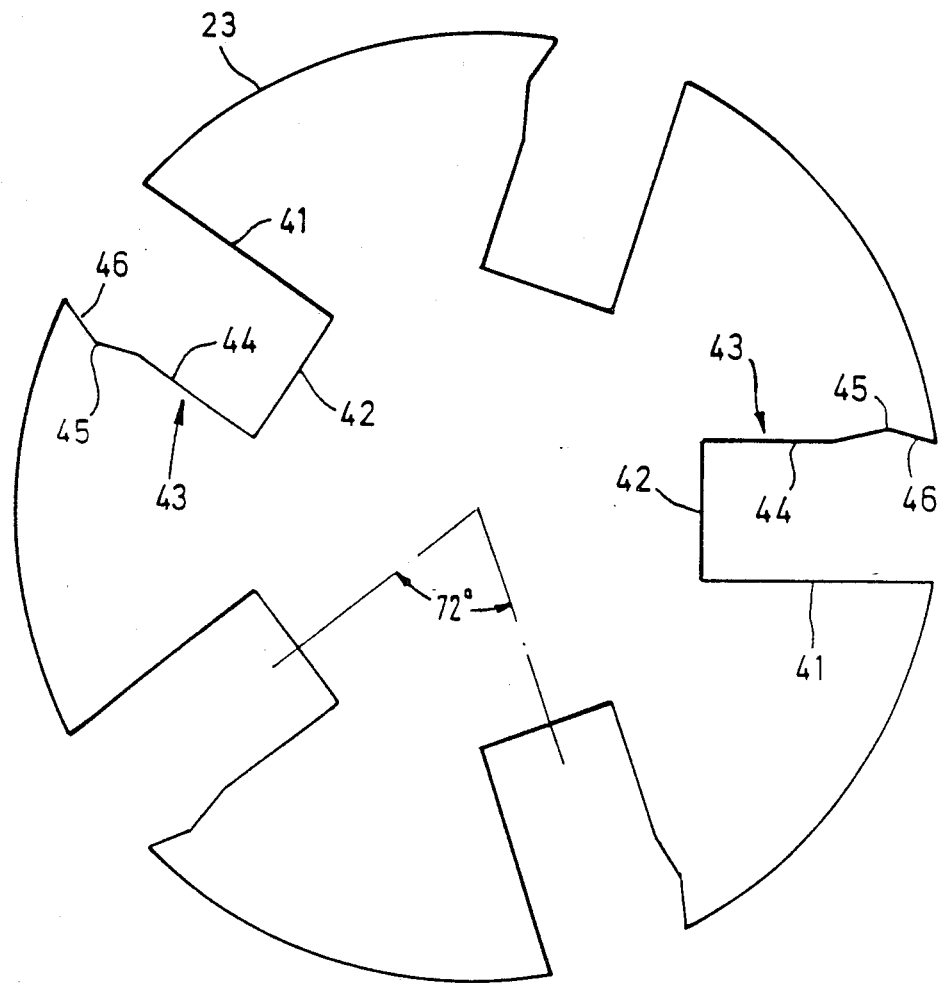
FIG. 2 is a detail of the conveyor shown in FIG. 1.

The conveyor disc 23 is illustrated in greater detail in FIG. 2. The disc is intended to rotate clockwise. Each radial slot has a straight leading edge 41 parallel to the radius of the disc through the center of the slot. It has an inner edge 42 at right angles to the leading edge. The trailing edge 43 of the slot has an inner portion 44 which is parallel to the leading edge and an outer portion 45 which is concave with its own outer portion 46 having a component facing toward the center of the disc and the center of the article. The concave V-shape of the outer portion 45 provides accurate radial location of the tablet to be carried in the slot since the center of the circular tablet will be held at the desired distance from the center of the disc. This means that the thickness gauge 31 can be accurately located over the circular path traced out by the centers of the tablets. This accurate positioning in conjunction with the positioning of the tablet along the circular path in response to the weight measurement described above avoids errors caused by measurements being made at different portions of different tablets. The inward facing outer portion 46 of the concave portion 45 of the trailing edge 43 of the slot guides the tablet in the radial path without the need for a barrier outside the slot to prevent the tablet becoming lost out of the slot as the disc rotates. The concave portion of the trailing edge of the slot is sufficiently shallow to allow the tablet to be pushed towards the radially inner end 42 of the slot at the hardness testing station and the crushing ram 33 has free access to the slot which it would not have if there were a stationary barrier around the conveyor disc.

The thickness testing gauge and the clearing stage are both operated by a vertically orientated pneumatic cylinders, whereas the hardness testing station comprises a horizontal pneumatic cylinder with a strain gauge.

The microprocessor 28 evaluates the tests and prints the results. A keypad 51 is provided for operator intervention.

A modified conveyor disc 23, in particular having a modified radial slot configuration 25', is illustrated in FIGS. 3A-E. This modified arrangement enables improved longitudinal axis capsule alignment to be achieved, which is advantageous for operation of the hardness tester station 32. FIGS. 3A-E illustrate the improved sequence of operation for longitudinal axis capsule crushing which can be achieved.

The configuration of the modified radial slots 25' is similar to that of radial slots 25 shown in FIG. 2. Namely, the radial slot 25' comprises a straight leading edge 41', a flat radially inner end 42' and a convex trailing edge 45'. The convex trailing edge 45' is V-shaped with an inward facing portion 46'. Thus, it will be apparent that the modified radial slot 25' corresponds to radial slot 25 with the omission of the inner portion 44 of trailing edge 43, and a corresponding reduction in the length of the leading edge 41.

As previously described, the conveyor disc 23 primarily moves in a clockwise direction, with capsule alignment being assisted by small anti-clockwise movements of the conveyor disc. It is assumed that when a radial slot 25' arrives opposite the hardness tester station 32 the tablet or capsule 20 is randomly positioned within the radial slot. This may not normally be the case, but the alignment procedure assumes that the tablet is initially randomly positioned in order to cope with any unusual circumstances in which the tablet is rndomly positioned.

Figure 3A:
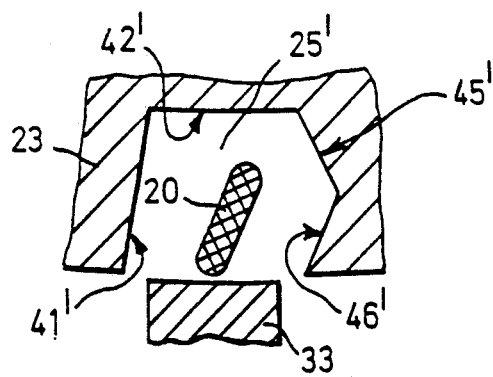
FIGS. 3A-E illustrate the sequence of operation at the hardness testing station 32 when use is made of a conveyor disc having a modified configuration for the radial slots.
Figure 3B:
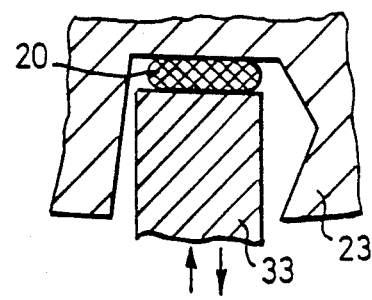

Radial alignment of a slot 25' with the crushing ram 33 and random orientation of the tablet is illustrated in FIG. 3A. Rotation of conveyor disc 23 is inhibited and crushing ram 33 reciprocates within the slot 25' in order to orientate the tablet 20 with one flat face parallel to and in contact with the radially inner end 42' of the slot 25'. This is illustrated in FIG. 3B.

Clearly, information concerning the thickness of the tablet is required in order to correctly limit the extent of the reciprocating motion of ram 33 within slot 25'. In the arrangement described with respect to FIG. 1, information concerning the thickness of the tablet 20 is obtained from the microprocessor 28, in which the information was stored as the result of the measurement conducted by the thickness gauge 29.

Figure 3C:
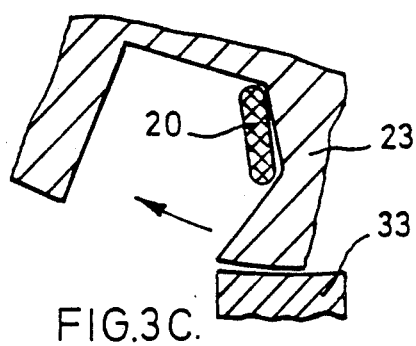
Figure 3D:
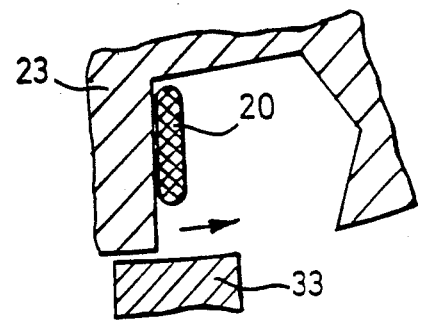
Figure 3E:
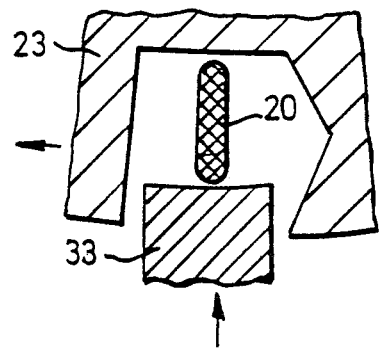

After the tablet has been located against surface 42', ram 33 is withdrawn from slot 25' and the conveyor disc 23 is rotated in a clockwise direction through a predetermined angular distance. The effect of this rotation is to align the tablet 20 in the V-shaped trailing edge 45' of the slot 25'. As previously described, the inwardly facing portion (46) prevents the tablet 20 from escaping from the slot 25'. This alignment of the tablet 20 in the V-shaped portion 45' is illustrated in FIG. 3C.

Subsequently, the conveyor disc 23 is rotated counterclockwise through a predetermined angular distance. This has the effect of locating the tablet 20 with one of its flat faces parallel to and in contact with the straight leading edge 41' of slot 25'.

Finally, conveyor disc 23 is rotated a short distance in the clockwise direction so as to leave tablet 20 longitudinally aligned with ram 33 and out of contact with both the leading and trailing edges of the radial slot 25'. Ram 33 can now again move into slot 25' and thereby effect the required longitudinal axis crushing of tablet 20.

The measurement to be made is the force applied to the ram in order for the tablet to crush. A displacement transducer may be used to confirm that the distance travelled by ram 33 is consistent with a longitudinal crush rather than a widthwise crush. Microcomputer 28 thereby accepts or rejects the test result.

Figure 4:
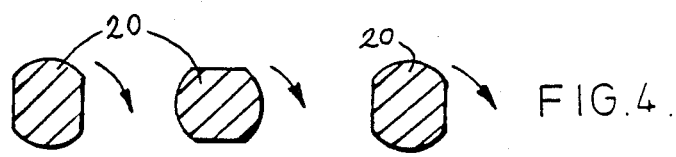
FIG. 4 illustrates how a particular form of capsule tends to roll when transported on an index wheel table.

It is common for tablets to have width and thickness dimensions which are of similar values and often tablets will have two flat parallel faces joined by corresponding convex surfaces at either end. A consequence of this conventional tablet shape is that the tablets tend to roll when transported on a conveyor disc. This tablet configuration and resulting tendency to roll is illustrated in FIG. 4 of the drawings. Such rolling motion of the tablet results in difficulties when conducting automated thickness testing, especially when the thickness has to be measured across the convex surfaces rather than across the flat surfaces. FIGS. 5 and 6 illustrate an arrangement which enables reliable alignment of tablets for convex surface thickness measurement.

Figure 5A:
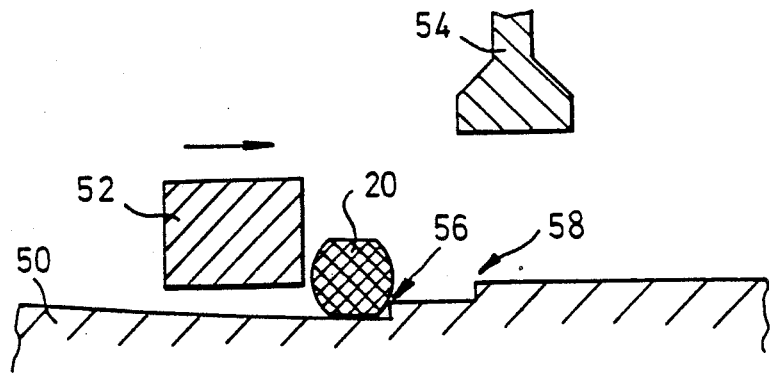
FIGS. 5A-C illustrate the sequence of operation for aligning the shaped capsule shown in FIG. 4, starting from a first capsule orientation.
Figure 5B:
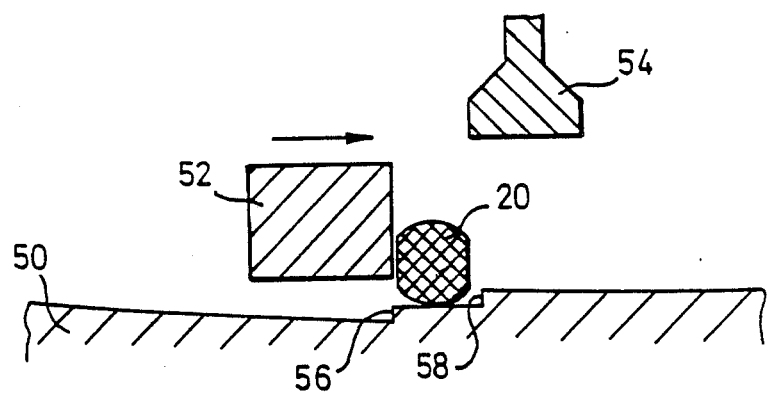
Figure 5C:
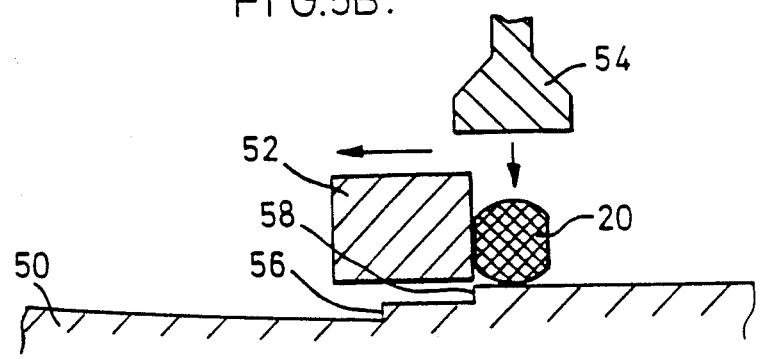
Figure 6A:
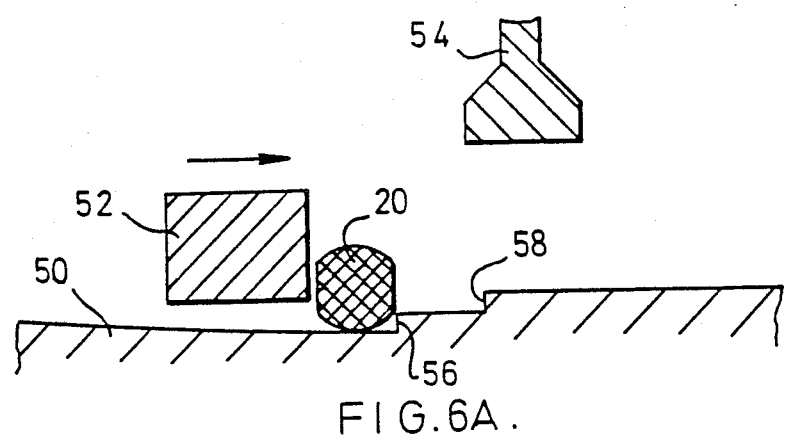
FIGS. 6A-C illustrate the sequence of operations for aligning the shaped capsule shown in FIGS. 4 and 5, starting from a second capsule orientation.
Figure 6B:
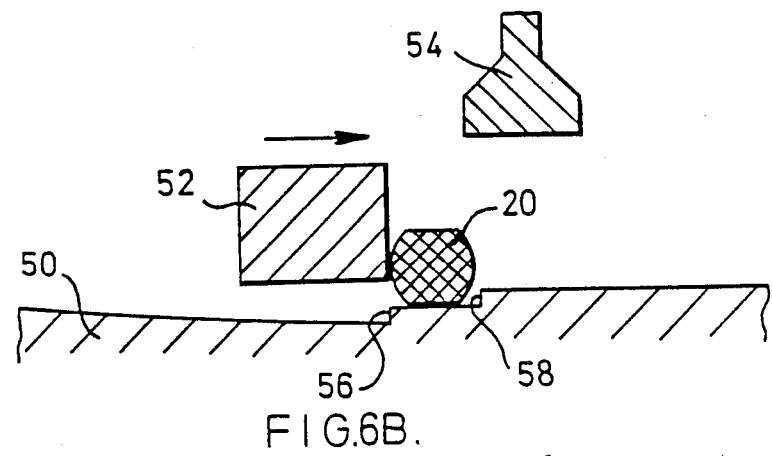
Figure 6C:
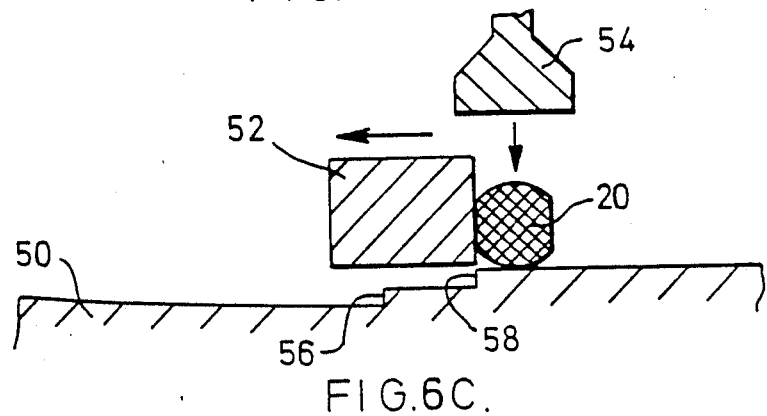

The arrangement illustrated in FIGS. 5 and 6 include an index table 50, an index wheel 52 and a thickness gauge head 54. These components are conventional apart from the fact that the index table 50 is provided with two steps, 56 and 58. The index table 50 is stationary and the gauge 54 reciprocates toward and away from the table 50. Steps 56 and 58 are located, in the illustrated arrangement, to the left of the axis on which the gauge head 54 reciprocates. Progressing from left to right in the illustrated arrangement, that is in the direction of counterclockwise motion of index wheel 52, steps 56 and 58 successively reduce the distance (taken along the reciprocating axis of head 54) between the table and the head. The respective heights of steps 56 and 58 together with the separation between index wheel 52 and table 50 are determined in accordance with the configuration of the tablets to be tested. These dimensions are selected to ensure the sequence of operation as illustrated in FIGS. 5A–C or 6A–C. Two sequences illustrate the operation from the two possible initial orientations of tablet 20 on table 50.

Assuming that the initial orientation of tablet 20 is such that it has a flat surface in contact with table 50, subsequent movement of the tablet is as depicted in FIG. 5. FIG. 5A illustrates index wheel 52 having moved tablet 20, with a flat surface in contact with table 50, over the table until the leading convex edge encounters step 56. Since the height of step 56 is less than the radial separation between table 50 and wheel 52, and both distances are less than the width between the flat surfaces of the tablet, continued counterclockwise rotation of wheel 52 causes tablet 20 to roll through 90°. As a result, the tablet sits on top of step 56 with the previously leading convex edge in contact with the top of the step.

The cumulative height of steps 56 and 58 is less than the radial separation between table 50 and head 54. Most importantly, the height of step 58 is less than the separation between the leading edge of the tablet and the top of step 56, which separation results from the convex surface of the tablet. This is illustrated in FIG. 5B. As a consequence of the described dimensions, continued counterclockwise rotation of wheel 52 does not cause tablet 20 to rotate but instead the convex surface thereof rides up over step 58 so that the tablet becomes positioned beneath gauge head 54, with the flat surfaces of the tablet aligned parallel to the axis of reciprocation of the head. Index wheel 52 is now rotated clockwise so as to leave tablet 20 for thickness testing across the convex surfaces thereof, by reciprocating movement of head 54, as illustrated in FIG. 5C.

Assuming that a convex surface of tablet 20 is initially in contact with table 50, in contrast to the initial orientation shown in FIG. 5A, the operating sequence is as depicted in FIGS. 6A–C. As shown in FIG. 6A, the tablet 20 is moved across table 50 by index wheel 52 with a convex surface of the tablet in contact with the table, until the tablet reaches step 56. The height of step 56 is such that the extreme end of the flat surface of the tablet comes into contact with the leading edge of step 56. Continued counterclockwise rotation of wheel 52 has the consequence that tablet 20 rolls through 90° so that the flat surface thereof is brought into contact with the top of step 56. This is illustrated in FIG. 6B. Further counterclockwise motion of index wheel 52 brings the leading convex surface of the tablet into contact with step 58. The continued motion causes the tablet again to roll through 90°, so that the convex surface comes into contact with the top of step 58. The tablet 20 is thus aligned between table 50 and gauge head 54 with the flat surfaces of the tablet parallel to the axis of reciprocation of head 54. This is illustrated in FIG. 6C. Finally, index wheel 52 is rotated clockwise and gauge head 54 reciprocated so as to measure the thickness of tablet 20 across the convex surfaces thereof.

From the above description given with reference to FIGS. 5 and 6, it will be appreciated that the described and illustrated configuration of the arrangement is such as to ensure that the tablet is always aligned between the table 50 and gauge head 54 for thickness testing across the convex surfaces of the tablet.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. Apparatus for measuring the thickness dimension of an article having thickness and radial dimensions, the apparatus comprising:

a sensor arranged to be moved along said thickness dimension to contact the article;

means for centering the article under said sensor, said centering means including:

(a) weighing means for weighing the article and for producing a measured weight signal thereof; and (b) calculating means for calculating a radial dimension for said article on the basis of said measured weight and a standard thickness associated with said article;

said centering means being responsive to said calculated radial dimension to move and center said article under said sensor; and means for measuring the position of said sensor when in contact with the article and producing an output indicative of said thickness dimension.

2. Apparatus as claimed in claim 1, wherein said calculating means is responsive to the square root of said measured weight.

3. Apparatus as claimed in claim 1, wherein said means for centering further comprises a conveyor for moving articles in a circular path, the conveyor comprising a disc formed with radial slots moveable with the disc past of the sensor and past the weighing means, each slot having a pushing edge for pushing an article located in the slot when the disc is rotated in a forward direction, said pushing edge having a concave portion suitable for engaging the article therewith and an inward facing portion in the concave portion for retaining said article in said slot and for entraining the article on said circular path.

4. Apparatus as claimed in claim 3, wherein said concave portion is V-shaped.

5. Apparatus as claimed in claim 3, further comprising a plurality of processing stations, the conveyor being moved step-wise to convey the articles step-wise between said processing stations.

6. An apparatus as claimed in claim 5, wherein said processing stations include a station for crushing said article.

7. An apparatus as claimed in claim 6, wherein said processing stations include a receiving station for receiving said articles within said disc.

8. An apparatus as claimed in claim 6, wherein said processing stations include a weighing station, said weighing means being located at said weighing station.

* * * * *